(12) United States Patent
Mestl et al.

(10) Patent No.: US 11,097,254 B2
(45) Date of Patent: Aug. 24, 2021

(54) SYNTHESIS OF A MOVNBTE CATALYST HAVING A REDUCED NIOBIUM AND TELLURIUM CONTENT AND HIGHER ACTIVITY FOR THE OXIDATIVE DEHYDROGENATION OF ETHANE

(71) Applicant: Clariant Produkte (Deutschland) GmbH, Frankfurt am Main (DE)

(72) Inventors: Gerhard Mestl, Munich (DE); Klaus Wanninger, Kolbermoor (DE); Daniel Melzer, Munich (DE); Maria Cruz Sanchez-Sanchez, Munich (DE); Julia Tseglakova, Muehlheim an der Ruhr (DE); Johannes Lercher, Ottobrunn (DE)

(73) Assignee: CLARIANT PRODUKTE (DEUTSCHLAND) GMBH, Frankfurt am Main (DE)

( * ) Notice: Subject to any disclaimer, the term of this patent is extended or adjusted under 35 U.S.C. 154(b) by 0 days.

(21) Appl. No.: 16/479,702

(22) PCT Filed: Jan. 26, 2018

(86) PCT No.: PCT/EP2018/052011
§ 371 (c)(1),
(2) Date: Jul. 22, 2019

(87) PCT Pub. No.: WO2018/141652
PCT Pub. Date: Aug. 9, 2018

(65) Prior Publication Data
US 2020/0061583 A1  Feb. 27, 2020

(30) Foreign Application Priority Data

Jan. 31, 2017 (DE) .......................... 102017000862.0

(51) Int. Cl.
*B01J 23/22* (2006.01)
*B01J 23/00* (2006.01)
(Continued)

(52) U.S. Cl.
CPC ............. *B01J 23/22* (2013.01); *B01J 23/002* (2013.01); *B01J 23/28* (2013.01); *B01J 31/04* (2013.01);
(Continued)

(58) Field of Classification Search
CPC . B01J 23/22; B01J 23/002; B01J 23/28; B01J 27/00576; B01J 31/04;
(Continued)

(56) References Cited

U.S. PATENT DOCUMENTS

| 5,281,745 A | 1/1994 | Ushikubo |
| 5,380,933 A | 1/1995 | Ushikubo |

(Continued)

FOREIGN PATENT DOCUMENTS

| EP | 0318295 | 5/1989 |
| EP | 1930074 | 6/2008 |

(Continued)

OTHER PUBLICATIONS

Desanto, Peter, Structural aspects of the M1 and M2 phases . . . Z. Kristallogr. 219 (2004) 152-165.
(Continued)

*Primary Examiner* — Patricia L. Hailey

(57) ABSTRACT

A novel mixed oxide material is disclosed which contains molybdenum, vanadium, tellurium and niobium and the use of the molybdenum mixed oxide material as catalyst for the oxidative dehydrogenation of ethane to ethene or the oxidation of propane to acrylic acid and a process for producing the mixed oxide material.

17 Claims, 13 Drawing Sheets

X-ray diffraction pattern of the catalyst of example 1

(51) Int. Cl.
- *B01J 23/28* (2006.01)
- *B01J 31/04* (2006.01)
- *B01J 31/22* (2006.01)
- *B01J 35/00* (2006.01)
- *C07C 5/32* (2006.01)
- *C07C 5/48* (2006.01)
- *C07C 253/24* (2006.01)
- *C07C 255/08* (2006.01)

(52) U.S. Cl.
CPC ......... *B01J 31/2226* (2013.01); *B01J 35/002* (2013.01); *C07C 5/322* (2013.01); *C07C 5/48* (2013.01); *C07C 253/24* (2013.01); *C07C 255/08* (2013.01)

(58) Field of Classification Search
CPC .. B01J 31/2204; B01J 31/2226; B01J 35/002; B01J 35/1014; B01J 2523/56; B01J 2523/57; B01J 2523/64; C07C 5/322; C07C 5/48; C07C 253/24; C07C 255/08; C01P 2002/72
USPC ......... 502/311, 312, 215; 585/654; 558/466; 562/542, 546, 547, 549
See application file for complete search history.

(56) References Cited

U.S. PATENT DOCUMENTS

| | | | |
|---|---|---|---|
| 6,656,873 | B2 | 12/2003 | Chaturvedi |
| 6,867,328 | B2 | 3/2005 | Borgmeier |
| 7,009,075 | B2 | 3/2006 | Hazin |
| 7,038,082 | B2 | 5/2006 | Borgmeier |
| 7,053,022 | B2 | 5/2006 | Gaffney |
| 9,073,036 | B2 | 7/2015 | Hagemeyer |
| 2003/0013904 | A1 † | 1/2003 | Chaturvedi |
| 2003/0088118 | A1 * | 5/2003 | Komada ............... C07C 253/24 558/332 |
| 2003/0187299 | A1 * | 10/2003 | Machhammer ....... C07C 51/252 562/547 |
| 2004/0063990 | A1 * | 4/2004 | Gaffney ................ C07C 51/215 558/322 |
| 2004/0082190 | A1 * | 4/2004 | Borgmeier ........... B01J 27/0576 438/722 |
| 2008/0200716 | A1 * | 8/2008 | Lugmair .............. B01J 27/0576 558/319 |
| 2010/0255985 | A1 * | 10/2010 | Gaffney ................... C07C 5/48 502/312 |
| 2010/0255986 | A1 * | 10/2010 | Gaffney ............... B01J 37/0036 502/312 |
| 2010/0256432 | A1 * | 10/2010 | Arnold ...................... C07C 5/48 585/655 |
| 2015/0119622 | A1 * | 4/2015 | De Rooij ............... B01J 23/002 585/658 |
| 2015/0148563 | A1 † | 5/2015 | Hagemeyer |
| 2016/0038922 | A1 * | 2/2016 | De Rooij ................. B01J 37/08 585/658 |
| 2019/0240647 | A1 * | 8/2019 | Gao ........................ B01J 23/22 |
| 2019/0366311 | A1 * | 12/2019 | Mestl ..................... B01J 37/036 |
| 2020/0061583 | A1 * | 2/2020 | Mestl ..................... B01J 37/033 |
| 2020/0139349 | A1 * | 5/2020 | Mestl ...................... B01J 23/28 |
| 2020/0215516 | A1 * | 7/2020 | Mestl ................... B01J 35/1019 |
| 2020/0290026 | A1 * | 9/2020 | Mestl ....................... B01J 37/04 |

FOREIGN PATENT DOCUMENTS

| | | |
|---|---|---|
| JP | 0723071 | 9/1995 |
| JP | 08226796 | 9/1996 |
| WO | 2005120702 | 12/2005 |
| WO | 2009106474 | 9/2009 |

OTHER PUBLICATIONS

Valente, Jamie S., Chemical, Structural, and Morphological Changes of a MoVTeNb catalyst . . . ACS Catal. 4, (2014) 1292-1301.
Sanfiz, A. Celaya, Preparation of Phase-Pure M1 MoVTeNb Oxide . . . Top. Catal. 50, (2008) 9-32.
Vitry, D., Mo—V—Te—(Nb)—O mixed metal oxides prepared by hydrothermal . . . Applied Catalysis A General 251 (2003) 411-424.
Ushikubo, Takashi Ammoxidation of propane over Mo—V—Nb—Te mixed oxide catalysts, Studies in Surface Science and Catalysis 112 (1997) 473-480.
Ivars et al., Selective oxidation of short-chain alkanes over hydrothermally prepared MoVTeNbO catalysts, Topics in Catalysis, vol. 38, Nos. 1-3, pp. 59-67, published Jul. 2006.†
Ren, et al. Enhanced Reducibility of Mg-Doped MoVTeNbOx Mixed Oxide Catalysts for Propane Oxidation Reaction, Malaysian Journal of Analytical Sciences, vol. 20, No. 6, pp. 1299-1310, published in 2016.†

\* cited by examiner
† cited by third party

Figure 1: X-ray diffraction pattern of the catalyst of example 1
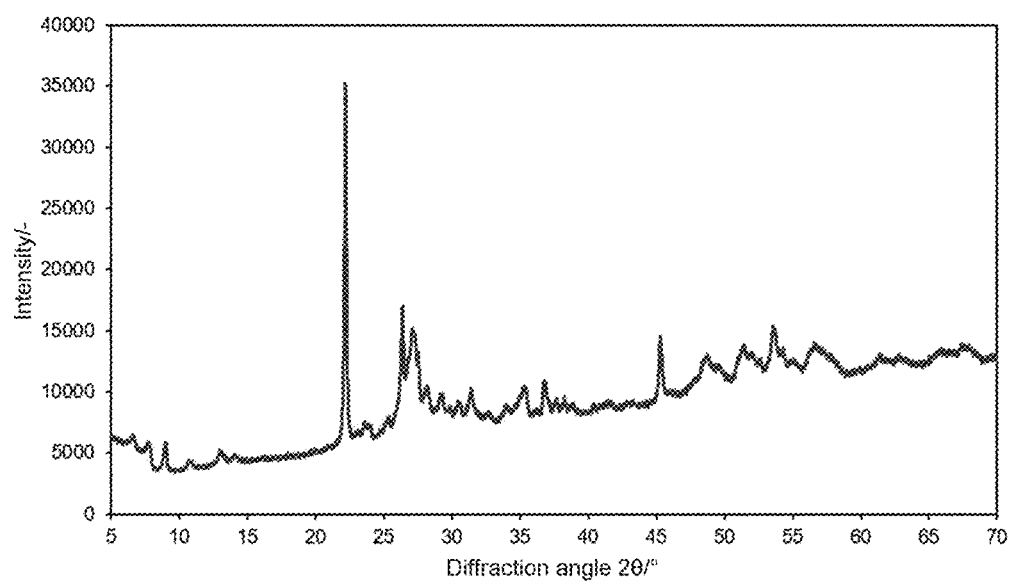

Figure 2: X-ray diffraction pattern of the catalyst of example 2
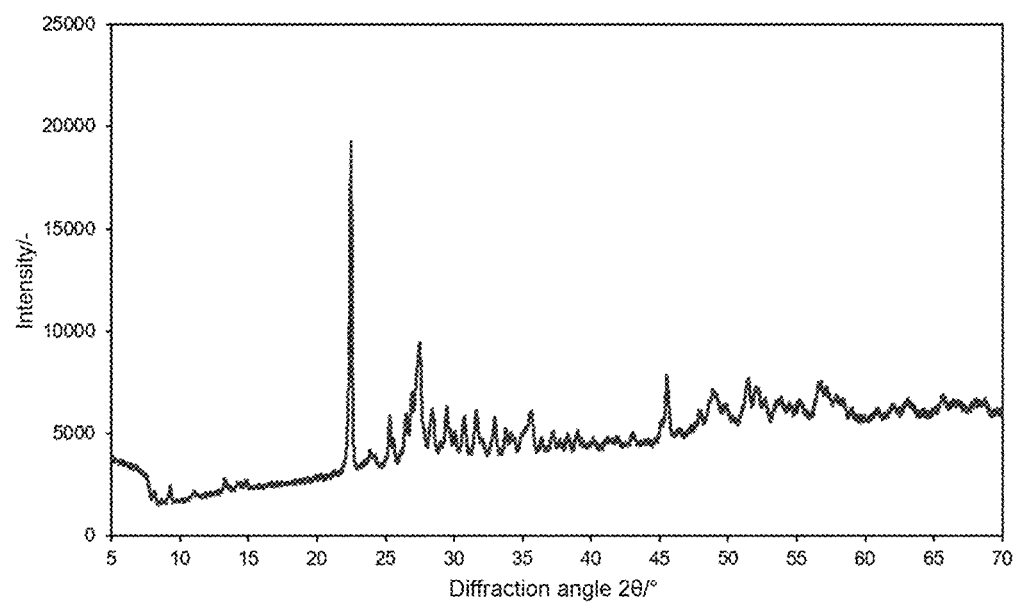

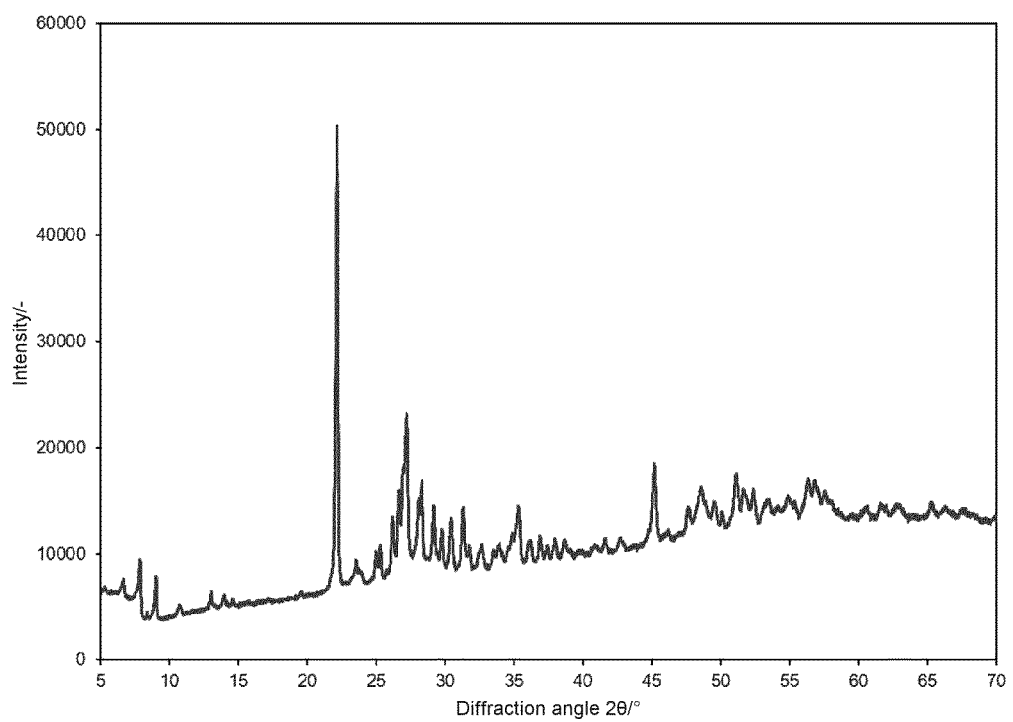
Figure 3: XRD of comparative example 1

Figure 4: XRD of comparative example 2
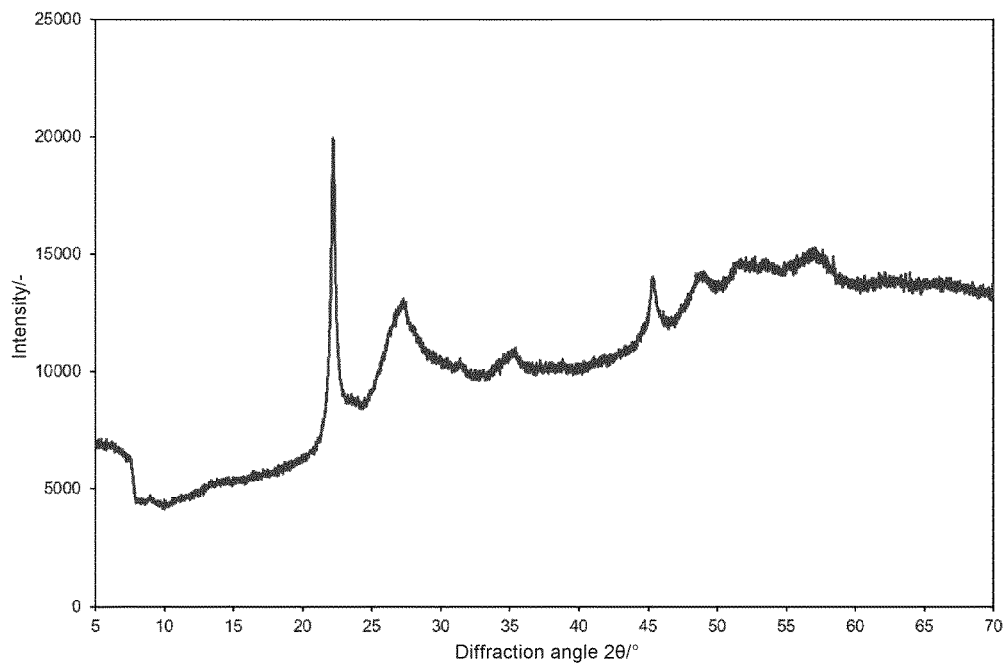

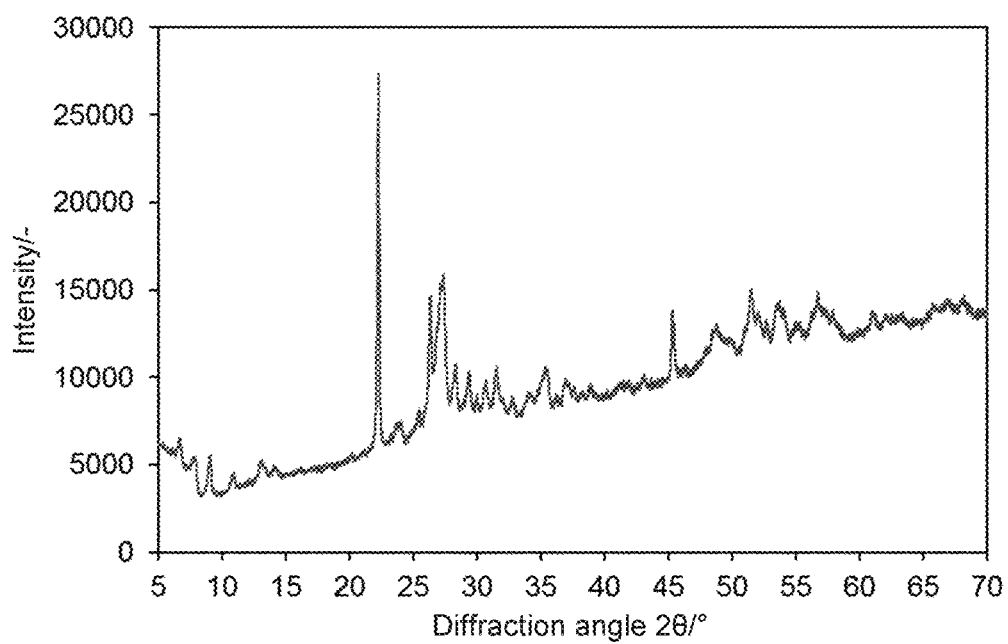
Figure 5: XRD of example 4

Figure 6: Scanning transmission electron micrograph of the catalyst of example 1
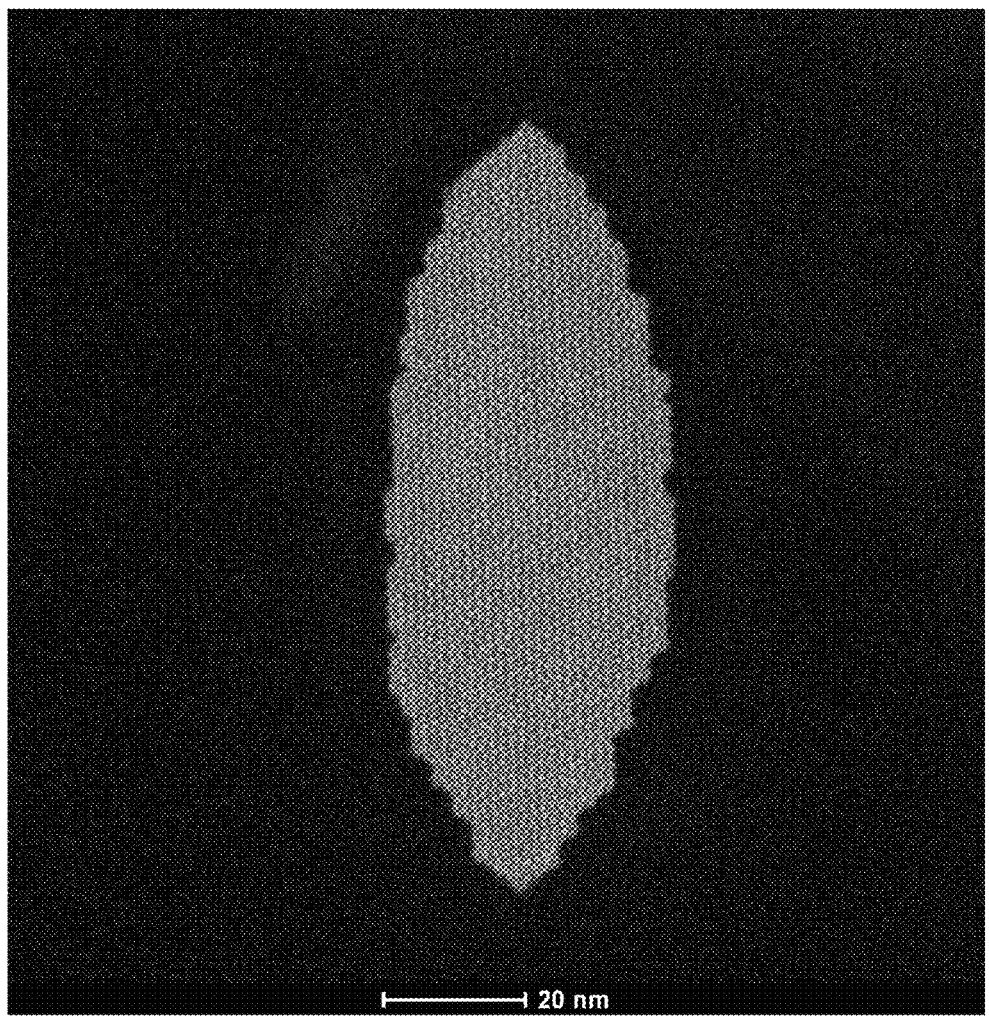

Figure 7: Scanning electron micrograph (secondary electron detector) of the catalyst of example 1
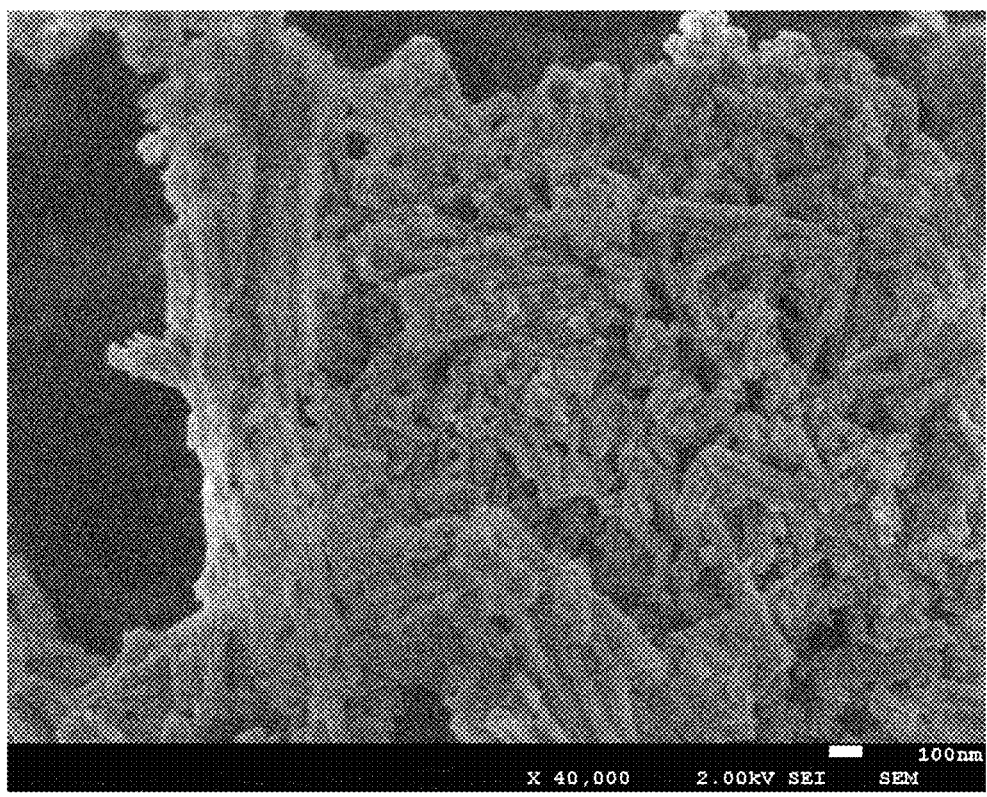

Figure 8: Pore size distribution of the catalyst of example 1
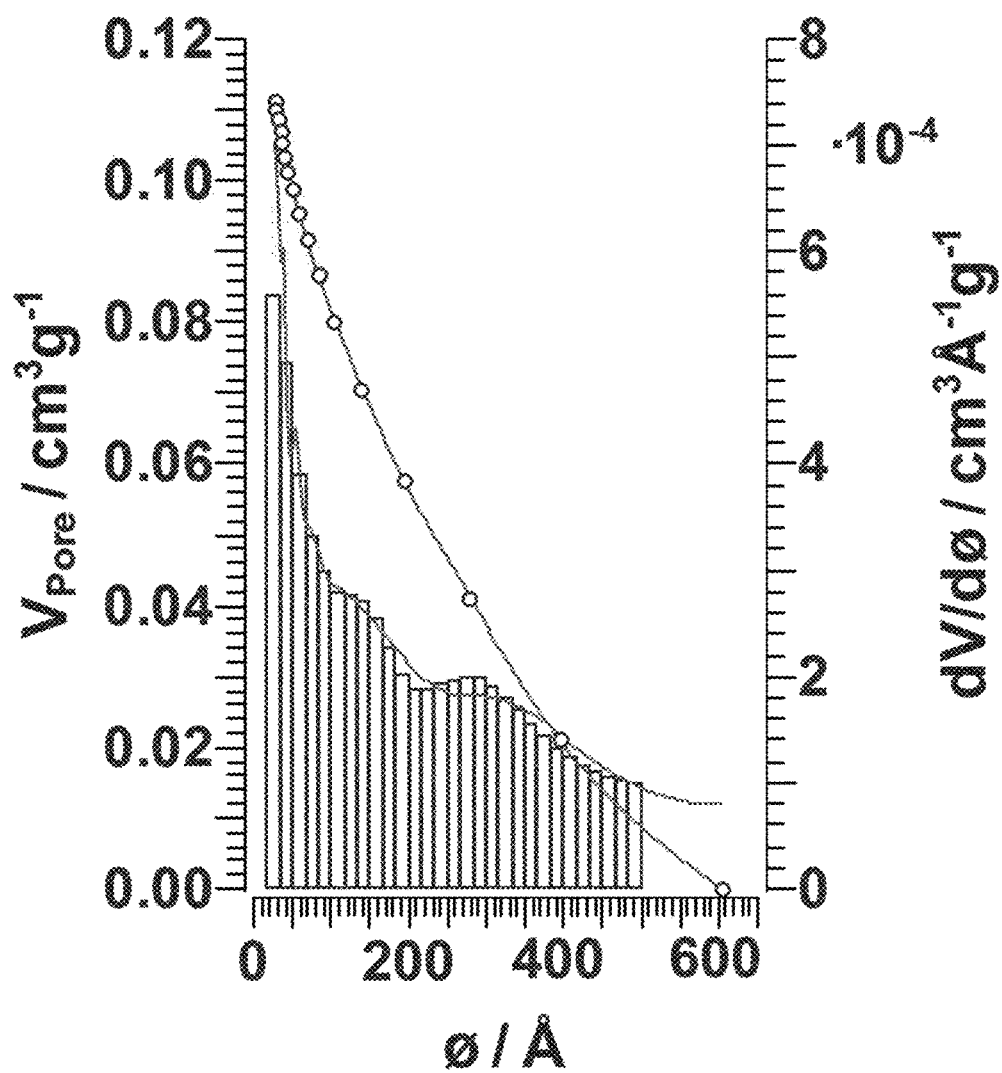

Figure 9: Pore size distribution of the catalyst of example 2
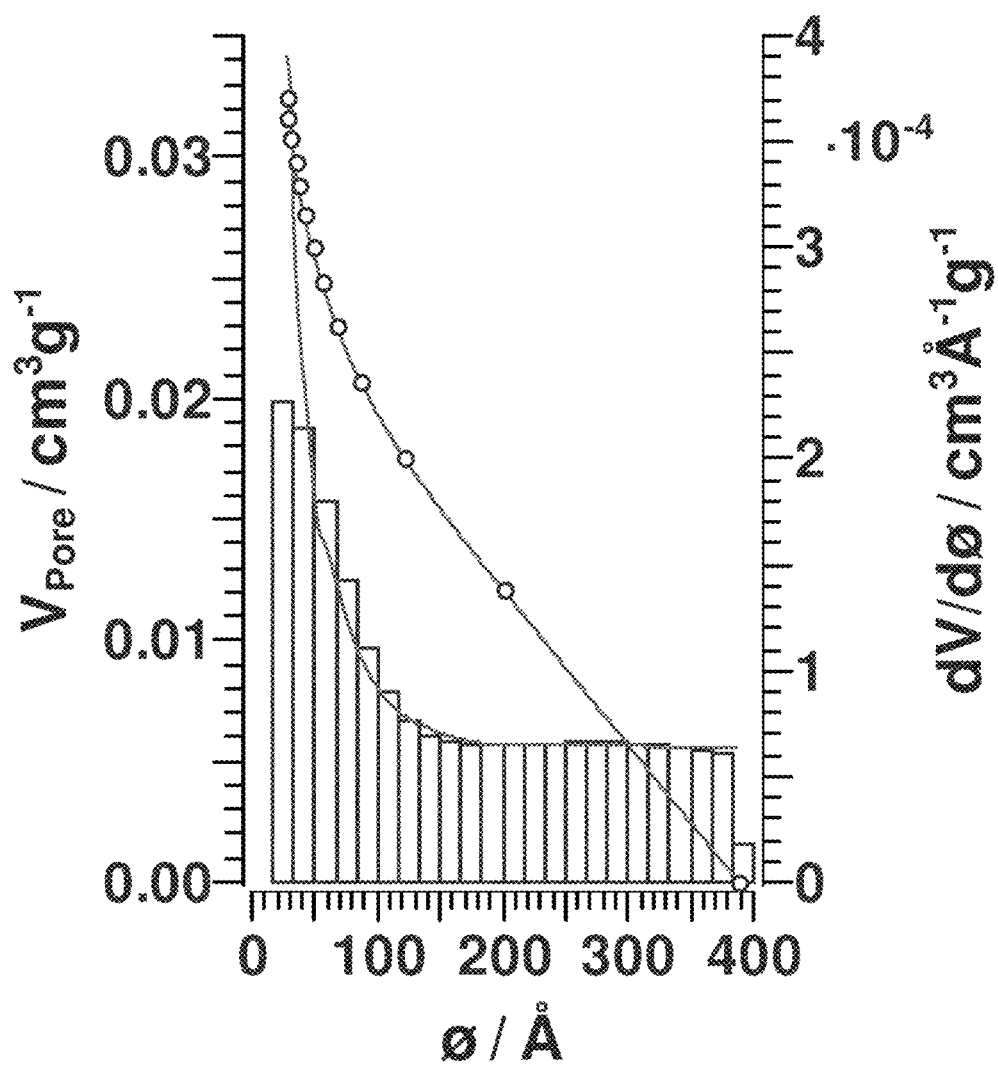

Figure 10: Pore size distribution of the catalyst of example 3
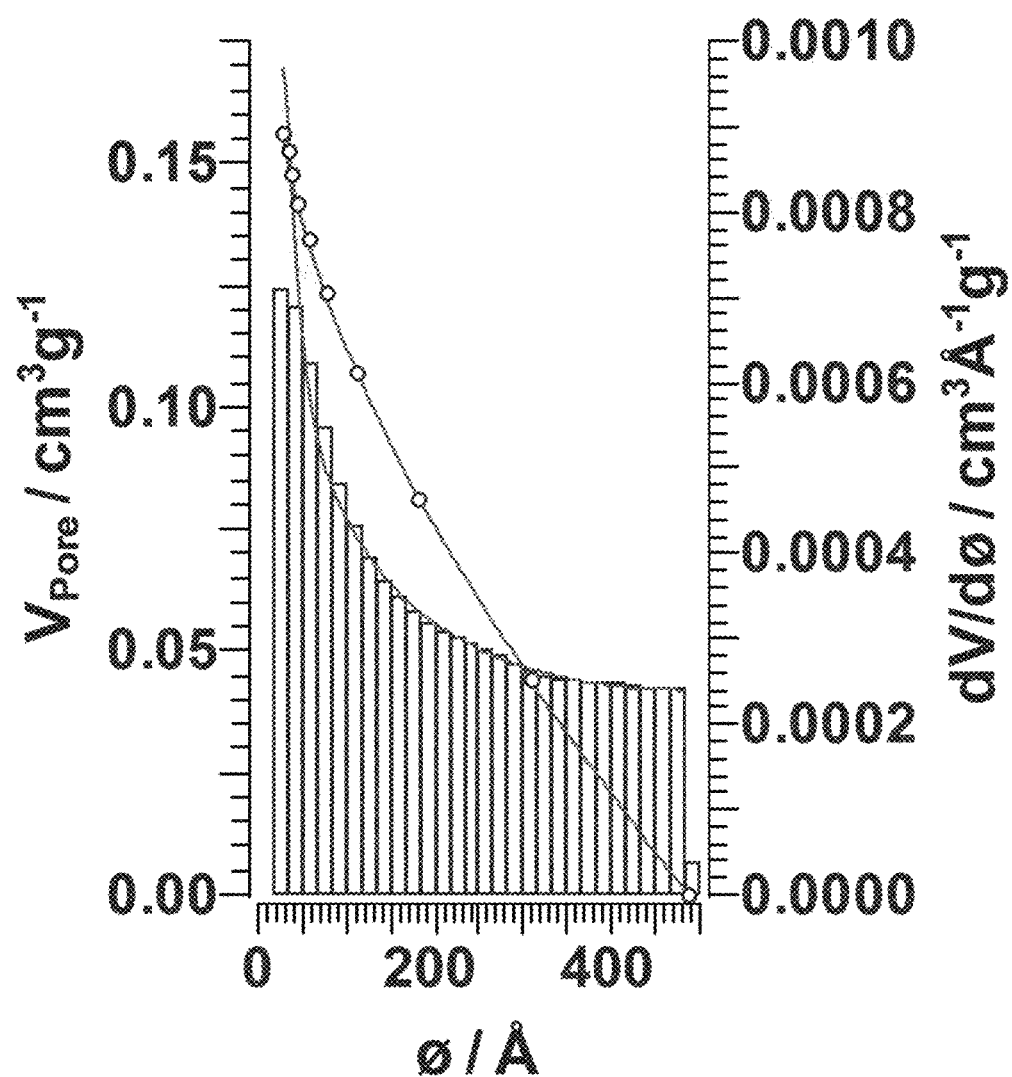

Figure 11: Ethane ODH activity of various catalyst examples
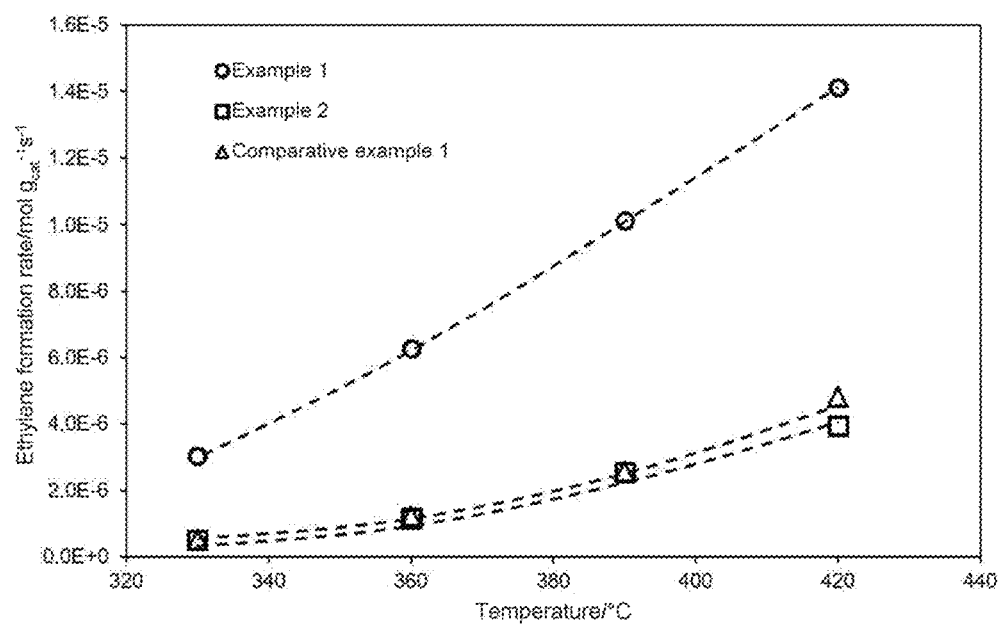

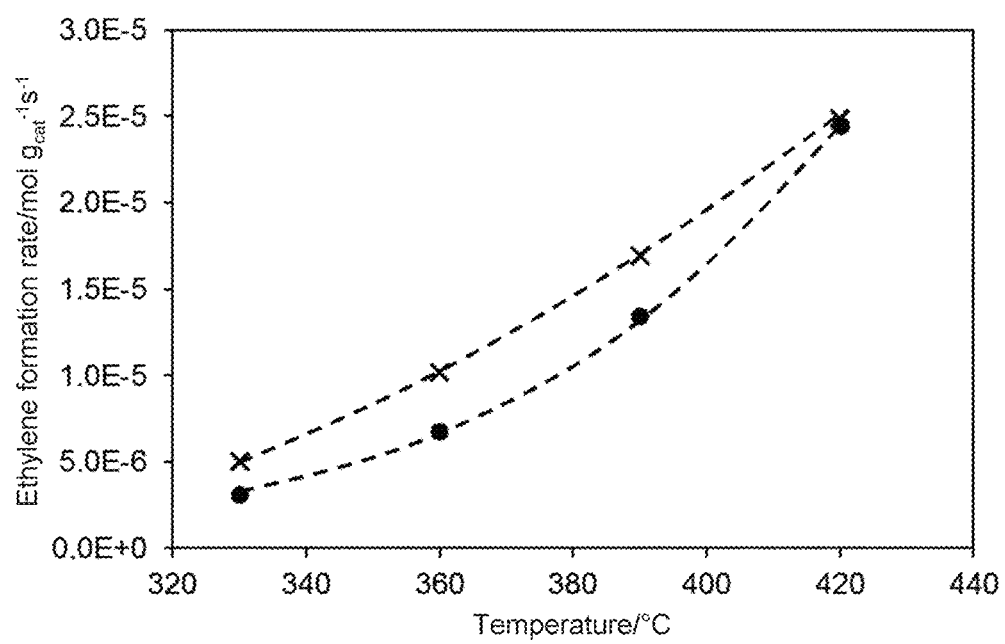
Figure 12: Ethane ODH activity of examples 4 and 5

Figure 13: XRD of example 5
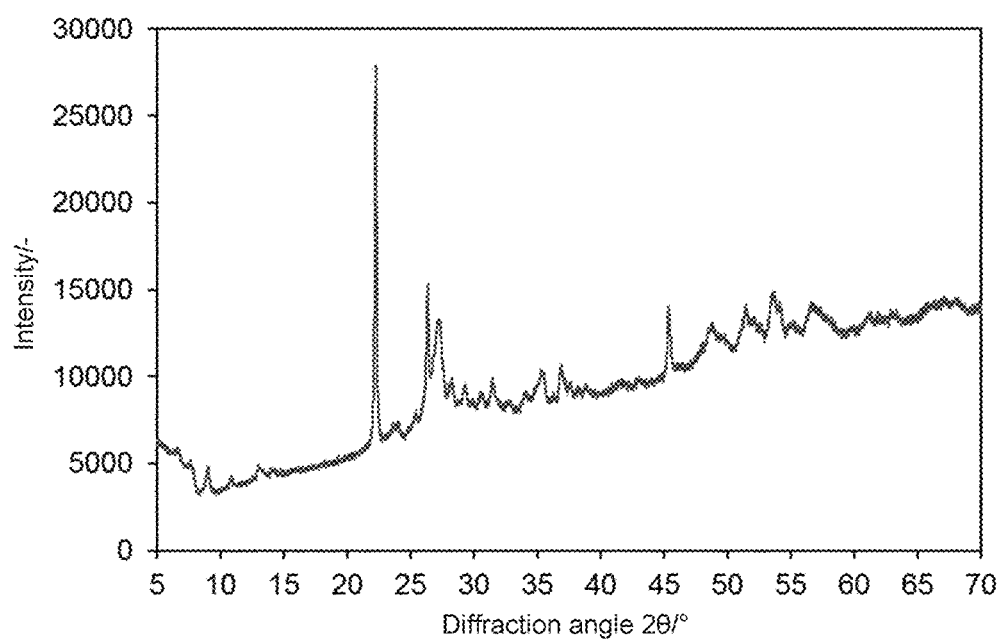

SYNTHESIS OF A MOVNBTE CATALYST HAVING A REDUCED NIOBIUM AND TELLURIUM CONTENT AND HIGHER ACTIVITY FOR THE OXIDATIVE DEHYDROGENATION OF ETHANE

The invention relates to a novel mixed oxide material which contains molybdenum, vanadium, tellurium and niobium and the use of the molybdenum mixed oxide material as catalyst for the oxidative dehydrogenation of ethane to ethene or the oxidation of propane to acrylic acid and a process for producing the mixed oxide material.

MoVNbTe mixed oxides for the oxidation of propane to acrylic acid, for the ammoxidation of propane to acrylonitrile or for the oxidative dehydrogenation of ethane to ethene are prior art. More than 200 patents and numerous scientific publications are concerned with catalysts based on MoVNbTe mixed oxides. The promotion of these mixed oxides with other metals of the Periodic Table is known. Here, the highest previously described acrylic acid yields are 60% and those of ethene are about 80%.

The MoVNbTe basis system based on four elements for a catalyst has been proposed by Mitsubishi for the ammoxidation of propane to acrylonitrile (1989, EP 318295 A2) and the oxidation to acrylic acid (1994, EP 608838 A2). JP H07-053414 (Mitsubishi) discloses a catalytic process for preparing ethylene by oxidative hydrogenation of ethane at low temperature, in high yield and with high selectivity. This process for preparing ethylene comprises contacting ethane with a gas containing molecular oxygen in the presence of a catalyst composition at elevated temperature, where the catalyst composition contains a mixed metal oxide which has molybdenum, vanadium, tellurium and oxygen as main components and displays an X-ray powder diffraction pattern which has essentially the following relative peak intensities: $2\theta(+-0.4°)$, rel. int.: $22.1°$ (100), $28.2°$ (400~3), $36.2°$ (80~3), $45.1°$ (40~3), $50°$ (50~3).

MoVNbTe catalysts consist mainly of two orthorhombic phases which are referred to as "M1" and "M2" (T. Ushikubo, K. Oshima, A. Kayou, M. Hatano, Studies in Surface Science and Catalysis 112, (1997), 473). The M1 phase appears to play the important role in the selective oxidation reactions.

According to P. De Santo et al., Z. Kristallogr. 219 (2004) 152, the main phases M1 and M2 in MoVNbTe mixed oxides for selective oxidation can be described, for example, by the following structural formulae:

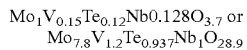
$Mo_1V_{0.15}Te_{0.12}Nb0.128O_{3.7}$ or
$Mo_{7.8}V_{1.2}Te_{0.937}Nb_1O_{28.9}$         M1

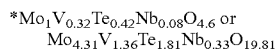
*$Mo_1V_{0.32}Te_{0.42}Nb_{0.08}O_{4.6}$ or
$Mo_{4.31}V_{1.36}Te_{1.81}Nb_{0.33}O_{19.81}$  M2

The two main phases can also occur with a somewhat different stoichiometry. Thus, both vanadium and molybdenum are present in the center of an octahedron of oxygen atoms and are therefore partly exchangeable in the structure, so that the same structure, e.g. the M1 phase, is also possible with a higher vanadium content. A detailed study of these relationships may be found in P. Botella et al., Solid State Science 7 (2005) 507-519. The M2 phase in particular is not active for the oxidative dehydrogenation of ethane. (See J. S. Valente et al., ACS Catal. 4(2014), 1292-1301, especially p. 1293). A catalyst consisting of very pure M1 phase is therefore desirable for the oxidative dehydrogenation of ethane. Attempts are therefore also made to produce these crystal phases cleanly and separately.

EP 529853 A2 discloses a catalyst which is suitable for preparing a nitrile from an alkane, wherein the catalyst has the empirical formula $MoV_bTe_cX_xO_n$, where X is at least one of Nb, Ta, W, Ti, Al, Zr, Cr, Mn, Fe, Ru, Co, Rh, Ni, Pd, Pt, Sb, Bi, B and Ce, b is from 0.01 to 1.0, c is from 0.01 to 1.0; x is from 0.01 to 1.0 and n is a number by means of which the total valence of the metallic elements is satisfied and the catalyst has X-ray diffraction peaks at the following $2\theta$ angles in its X-ray diffraction pattern: diffraction angle at $2\theta$ ($22.1°+/-0.3°$, $28.2°+/-0.3°$, $36.2°+/-0.3°$, $45.2°+/-0.3°$, $50.0°+/-0.3°$).

JP H07-232071 discloses a catalytic process for preparing a nitrile at a relatively low temperature and in a high yield, using an alkane as raw material and a particular catalyst. The main component of the catalyst is a mixed metal oxide composed of molybdenum, vanadium, tellurium, oxygen and X (X is one or more elements selected from the group consisting of niobium, tantalum, etc.), where the ratio of the main components, i.e. with the exception of oxygen, is expressed by the formulae I to IV: I) $0.25<rMo<0.98$, II) $0.003<rV<0.50$, III) $0.003<rTe<0.50$, IV) $0\leq rX<0.5$, (rMo, rV, rTe and rX are in each case the molar parts of molybdenum, vanadium, tellurium and X) and in the XRD displays XRD bands of this mixed oxide at the various $2\theta$ angles $9.0°\pm0.3°$, $22.1°\pm0.3°$, $27.3\pm0.3°$, $29.2°\pm0.3°$ and $35.4°\pm0.3°$. According to this document, a nitrile can be prepared in high yield at a low temperature by reacting an alkane without the presence of a halogenated substance, e.g. with water, etc., in the reaction system.

Other successful attempts to produce a pure M1 phase are based on dissolving the M2 phase out from the phase mixture. These experiments are described, for example, in EP 1301457 A2, EP 1558569 A1 or WO 2009106474 A2.

A. C. Sanfiz et al., Top. Catal. 50 (2008) 19-32, describe hydrothermal syntheses of MoVNbTe oxide. These syntheses start out exclusively from soluble compounds. Telluric acid $Te(OH)_6$ is generally used as soluble compound of tellurium. In the most readily available oxidic tellurium compound $TeO_2$, tellurium has the oxidation state +4. Unfortunately, tellurium dioxide ($TeO_2$) is sparingly soluble in water. Furthermore, the tellurium in telluric acid has the oxidation state +6. Tellurium therefore has to be oxidized up in the preparation of telluric acid. The most widespread synthesis is carried out by oxidation of tellurium oxide with hydrogen peroxide, which on a large scale is accompanied by safety problems because hydrogen peroxide can disproportionate into water and oxygen in a spontaneous decomposition. For this reason, telluric acid can be prepared in large amounts only with difficulty.

The Nb component used in the synthesis of MoVNbTe mixed oxides is generally ammonium niobium oxalate. Niobium oxide, on the other hand, is sparingly soluble and therefore has only limited suitability as starting compound.

Watanabe (Applied Catal. A General, 194-195 (2000) 479-485) describes, inter alia, the hydrothermal synthesis from the sparingly soluble precursors $MoO_3$, $V_2O_5$ and $TeO_2$. The hydrothermal synthesis gives a precursor for an ammoxidation catalyst which compared to a catalyst produced by the known dry method has twice the activity after calcination. The mixed oxides produced by a solid-state reaction display a rather low activity. It has been proposed that the higher activity of the catalyst produced by the hydrothermal synthesis is due first and foremost to the higher surface area.

D. Vitry et al. Applied Catalysis A: General 251 (2003) 411-424 report a mixed oxide having the stoichiometry $Mo_1V_{0.25}Nb_{0.11}Te_{0.11}O_x$. In more recent studies on the oxidative dehydrogenation (ODH) of ethane, use was made of catalysts having the stoichiometry $Mo_1V_{0.3}Nb_{0.10}Te_{0.10}O_x$.

D. Melzer et al. *Angew. Chem. Int. Ed.* 55 (2016) 8873-8877), see "supplemental material" sample B) reports a mixed oxide having a high content of the M1 phase and an analyzed stoichiometry of $Mo_1V_{0.27}Nb_{0.10}Te_{0.08}O_x$.

One possible way of reducing the costs is to reduce the amount of niobium and tellurium required. Another is to use cheaper starting materials.

WO 2005120702 A1 describes a process for the hydrothermal production of multimetal compositions consisting of Mo and V, essentially with exclusive use of starting materials from the group of oxides, oxide hydrates, oxy acids and hydroxides for the element constituents of the oxidic multimetal compositions, where part of the element constituents present in the starting materials has an oxidation number below the maximum oxidation number.

WO 2013021034 A1 relates to a catalyst material for the oxidation and/or oxidative dehydrogenation of hydrocarbons, in particular for the selective oxidation of propane to acrylic acid, comprising a) molybdenum (Mo), b) vanadium (V), c) niobium (Nb), d) tellurium (Te), e) manganese (Mn) and cobalt, in which the molar ratio of at least one element selected from among manganese and cobalt to molybdenum is in the range from 0.01 to 0.2, more preferably from 0.02 to 0.15 and particularly preferably from 0.03:1 to 0.1:1. Furthermore, a catalyst for the oxidation and/or oxidative dehydrogenation of hydrocarbons, use of the catalyst material or of the catalyst, a process for producing a catalyst material for the oxidation and/or oxidative dehydrogenation of hydrocarbons and a process for the selective oxidation of propane to acrylic acid are indicated.

WO 2008068332 A1 relates to new mesoporous mixed metal oxide catalysts and a process for the production thereof and also the use thereof as catalyst for the oxidation of hydrocarbons or partially oxidized hydrocarbons. In particular, the disclosure relates to mesoporous mixed oxide catalysts which contain at least two, preferably at least three, different metal species, where at least one of these belongs to the group of the transition metals, to a process for producing such a catalyst, comprising a production step via the "neutral template" route and a calcination step in a substantially oxygen-free atmosphere at a temperature in the range from 300 to 700° C., to the use of such catalysts as oxidation catalysts for the preparation of oxidized hydrocarbons and in particular for the selective oxidation or ammoxidation of propane to acrylic acid and acrylonitrile. A preferred catalyst comprises the elements Mo, V, Te and Nb.

In all the syntheses of the M1 phase described in the prior art, the M1 phase is only formed in a high-temperature treatment, typically above 500° C., under inert gas after the reaction of the starting materials. In the present invention, a synthesis method for preparing a highly pure M1 phase which dispenses with the concluding high-temperature treatment has been found.

It is an object of the present invention to provide a novel simplified and efficient synthetic route for preparing a mixed oxide material containing molybdenum, vanadium, tellurium and niobium ("MoVTeNb mixed oxide") which is present in high phase purity as M1 phase.

This object is achieved by a process for producing a mixed oxide material containing molybdenum, vanadium, tellurium and niobium, comprising the steps:
a) production of a mixture of starting compounds containing molybdenum, vanadium, niobium and a tellurium-containing starting compound in which tellurium is present in the oxidation state +4 and also oxalic acid and at least one further oxo ligand,
b) hydrothermal treatment of the mixture of starting compounds at a temperature of from 100 to 300° C. to give a product suspension,
c) isolation and drying of the mixed oxide material present in the suspension resulting from step b).

The mixture of starting compounds is preferably present as aqueous suspension and is subsequently hydrothermally treated. The term "hydrothermally" refers predominantly to reaction conditions for producing a catalyst material in the presence of water and at elevated temperature and/or elevated pressure, for example in an autoclave. Here, the pressure can be in the range from 5 to 30 bar, preferably from 10 to 27 bar. Illustrative pressure ranges are from 11 to 20 bar.

As a result of the hydrothermal treatment (step b)), a product suspension containing the MoVNbTe mixed oxide as solid is obtained. In the process of the invention, the isolation of the solid of the suspension, which represents the MoVNbTe mixed oxide according to the invention, in step c) can be carried out in one or more filtration steps, e.g. filtering-off of the mother liquor. Drying can be carried out in a single step or in two steps in flowing or static air. The first drying step is preferably carried out at from 60° C. to 150° C. (particularly preferably from 80° C. to 120° C.), and a second drying step can be carried out at from 200° C. to 400° C. In addition, step c) of the process of the invention can comprise one or more washing steps, calcination steps (thermal treatment) and/or milling steps. The calcination can be carried out at from 200 to 500° C., preferably from 250° C. to 350° C., in air.

After drying of the filtrate in step c), the dried mixture can optionally be activated, e.g. in a flowing or static inert gas atmosphere at from about 500 to 700° C. for at least 1 hour (step d)). A suitable inert gas is, in particular, nitrogen, helium or argon. Preference is given to carrying out activation in the range from 550 to 650° C. For example, activation can be carried out at about 600° C. for about 2 hours.

An important aspect here is that, in contrast to the known syntheses, activation after the hydrothermal synthesis is not required in the process of the invention. Furthermore, it is also of importance that the desired stoichiometry of V (up to 0.3 relative to Mo), niobium and tellurium can be determined beforehand in the synthesis in the case of this synthesis. Only extremely low concentrations of the ions remain in the mother liquor from the crystallization. The metals are incorporated precisely in the desired stoichiometry into the MoVNbTe mixed oxide.

The starting compounds are the molybdenum-, vanadium-, tellurium- and niobium-containing starting materials of the hydrothermal synthesis (precursor compounds). These each contain one or more of the elements molybdenum, vanadium, tellurium or niobium.

The molybdenum-containing starting compound can, for example, be an ammonium heptamolybdate or molybdenum trioxide, the vanadium-containing starting compound can, for example, be an ammonium metavanadate, vanadyl sulfate or vanadium pentoxide, the niobium-containing starting compound can, for example, be ammonium niobium oxalate or niobium oxalate or niobium oxide. The tellurium-containing starting compound according to the invention is one in which tellurium is present in the oxidation state +4, i.e. as tellurium(IV) cation, for example tellurium dioxide or a compound of the formula $M_x^{n+}TeO_3$ (where n=1 or 2 and x=2/n), where M is an alkali metal or alkaline earth metal, e.g. $Na_2TeO_3$. The tellurium-containing starting compound is particularly preferably tellurium dioxide which can be present in any degree of hydration.

An advantage of the production process of the invention is that a synthesis of the M1 phase from insoluble and inexpensive oxides is possible, e.g. $MoO_3$, $V_2O_5$, $Nb_2O_5$ and $TeO_2$ are used as starting compounds. As further oxo ligands (i.e. in addition to oxalic acid), dicarboxylic acids and diols and also organic compounds having two adjacent carbon atoms which each bear a hydroxy group have been found to be particularly useful. Preference is given to using a mixture of citric acid and glycol as further oxo ligand.

The oxalic acid should preferably be present in the mixture of the starting compounds in an Mo/oxalic acid ratio of from 1:0.01 to 1:1, preferably from 1:0.08 to 1:0.4, more preferably from 1:0.15 to 1:0.25.

The at least one further oxo ligand, or all further oxo ligands together, should preferably be present in the mixture of the starting compounds in an Mo/oxo ligand ratio of from 1:0.01 to 1:1, preferably from 1:0.025 to 1:0.2, more preferably from 1:0.05 to 1:0.1.

This synthesis surprisingly gives the M1 phase straight after hydrothermal synthesis and drying, without a high-temperature treatment at a temperature above 400° C. being necessary. Surprisingly, the amount of tellurium and niobium used can be significantly reduced when using this procedure, but the catalytically active M1 phase is nevertheless formed in high phase purity.

It has been found that when $MoO_3$, $V_2O_5$, $Nb_2O_5$ and $TeO_2$ are used together with citric acid, glycol and oxalic acid, the hydrothermal crystallization of M1 phase occurs successfully without subsequent calcination. Preference is given to no ammonium ions being present during the synthesis. The production process of the invention allows the synthesis of an MoVTeNb mixed oxide material containing the elements Mo, V, Te and Nb (MoVTeNb mixed oxide) which comprises the M1 phase with only relatively small amounts of niobium and/or tellurium.

It is therefore a further object of the present invention to discover an MoVTeNb mixed oxide which comprises M1 phase and a greatly reduced amount of niobium and tellurium and can be used as catalyst material and has very high activity for the oxidation of alkanes.

This object is achieved by a mixed oxide material comprising the elements molybdenum, vanadium, niobium and tellurium which in the XRD has diffraction reflections h, i, k and l whose peaks are approximately at the diffraction angles (2θ) 26.2°±0.5° (h), 27.0°±0.5° (i), 7.8°±0.5° (k) and 28.0°±0.5° (l), characterized in that it has the following stoichiometry:

$$Mo_1V_aNb_bTe_cO_n \quad (I)$$

a=0.2 to 0.35, b=greater than 0 to 0.08, preferably from greater than 0.01 to 0.08, c=greater than 0 to 0.08, preferably from greater than 0.01 to 0.08, n=an integer determined by the valence and abundance of the elements other than oxygen in (I).

Here, b is preferably in the range from 0.001 to 0.8, or from 0.01 to 0.5, and c is preferably in the range from 0.001 to 0.8 or from 0.01 to 0.5.

The mixed oxide material of the invention can be used as catalyst or catalyst material for the oxidation and/or oxidative dehydrogenation of hydrocarbons, in particular for the selective oxidation of ethane to ethylene.

The catalyst material produced by the process of the invention can be used in various ways in a commercial catalyst. For example, it can be processed by tableting to give catalyst pellets which can then be introduced into a reactor.

The catalyst material can be used in various chemical processes, for example, the dehydrogenation of ethane to ethene, the oxidation of propane to acrylic acid, and the ammoxidation of propane by means of ammonia to give acrylonitrile.

The catalyst material can be used in various chemical processes, for example, the dehydrogenation of ethane to ethene, the oxidation of propane to acrylic acid, and the ammoxidation of propane by means of ammonia to give acrylonitrile.

The catalyst material can also be processed together with a suitable binder to give an extrudate (pellets, shaped bodies, honeycomb bodies and the like). As binder, it is possible to use any binder material with which a person skilled in the art is familiar and which appears suitable. Preferred binders are, inter alia, pseudo-boehmite and also siliceous binders such as colloidal silicon oxide or silica sol.

The catalyst material can also be processed together with other components, preferably with a binder, particularly preferably with an organic binder, for example an organic adhesive, polymers, resins or waxes, to give a washcoat which can be applied to a metallic or ceramic support. Additional impregnation steps or calcination steps can optionally be carried out.

The MoVNbTe mixed oxide of the invention is used as catalyst material in the examples and will therefore sometimes be referred to as catalyst in the experimental part.

FIG. 1: X-ray diffraction pattern of the catalyst of example 1.

FIG. 2: X-ray diffraction pattern of the catalyst of example 2.

FIG. 3: X-ray diffraction pattern of the catalyst of comparative example 1.

FIG. 4: X-ray diffraction pattern of the catalyst of comparative example 2.

FIG. 5: X-ray diffraction pattern of the catalyst of example 4.

FIG. 6: STEM image of the catalyst of example 1, in which the crystal structure of the M1 phase can be seen.

FIG. 7: SEM image of the catalyst of example 1, in which the acicular crystal shape of the M1 phase can be seen.

FIG. 8: $N_2$ pore distribution of the catalyst of example 1.

FIG. 9: $N_2$ pore distribution of the catalyst of example 2.

FIG. 10: $N_2$ pore distribution of the catalyst of example 3.

FIG. 11: comparison of the catalytic activity of the catalysts of examples 1 and 2 in the oxidative dehydrogenation of ethane.

FIG. 12: ethane ODH activity of examples 4 and 5.

FIG. 13: X-ray diffraction pattern of the catalyst of example 5.

It can clearly be seen that the XRD of the catalyst according to the invention in FIG. 2 has the typical reflections of the M1 phase at (2θ=) 26.2°±0.5° (h), 27.0°±0.5° (i), 7.8°±0.5° (k) and 28.0°±0.5° (l) (when using Cu—Kα radiation), even though an Mo/Nb ratio of only 1:0.05 and an Mo/Te ratio of 0.05 are present. The reflections are somewhat broader than in the comparative examples in which a high-temperature treatment has taken place (FIG. 3). FIG. 4 shows that in comparative examples 1 and 2 without the high-temperature treatment, only the reflection at 22.5°, which indicates the plane spacing, can be clearly identified. Only after the high-temperature treatment (FIG. 3) does this catalyst display the typical reflections of the M1 phase.

FIG. 11 shows that the catalyst according to the invention of example 1 displays a higher activity in the oxidative dehydrogenation of ethane than those of the comparative examples.

It can clearly be seen that the uncalcined catalyst according to the invention of example 1 is significantly more active with only half as much niobium and tellurium. The calcined catalyst according to the invention having only half as much niobium and tellurium of example 2 is just as active as the prior art catalyst which has likewise been treated at high temperature in comparative example 1. However, it is significantly cheaper since less of the expensive metals niobium and tellurium are required.

Methods of Characterization:

To determine the parameters of the catalysts according to the invention, the following methods are used:

1. BET Surface Area:

The determination is carried out by the BET method of DIN 66131; a publication of the BET method may also be found in J. Am. Chem. Soc. 60,309 (1938). The measurements were carried out at 77 K on a Sorptomatic 1990 instrument. The sample was evacuated for 2 hours at 523 K before the measurement. The linear regression of the isotherms according to the BET method was carried out in a pressure range of $p/p_0$=0.01-0.3 ($p_0$=730 torr).

2. Chemical Analysis (ICP) with Digestion Method

Apparatus Used:
Multiwave GO microwave
Reaction vessel made of PTFE
Plastic tube 50 ml
ICP Spectro Arcos
Chemicals Used:
HF 40% AR
HCl 37% AR
Sulfuric acid 98% AR
Sulfuric acid 1:1

The sample was in each case finely milled before the analysis.

50 mg of sample were weighed into a reaction vessel and admixed with 2 ml of twice-distilled water, 2 ml of hydrofluoric acid, 2 ml of hydrochloric acid and the vessel was closed. The sample was subsequently subjected to the following microwave program:

step 1 10 min. to 100° C., 1 min. hold,
step 2 5 min. to 180° C., 20 min. hold.

0.1 ml of scandium standard are placed in a plastic tube and the digestion solution is then transferred and subsequently heated, made up to the mark and shaken.

All elements were detected on the Arcos ICP; the following basic settings were used:

plasma power: 1400 watt
cooling gas flow: 14 l/min
auxiliary gas flow: 1.4 l/min
atomizing gas flow: 0.8 l/min The standards are all adapted with acid and the concentration by mass of scandium is 2 mg/l.

Standards:
Mo 300/400/500 mg/l
Nb 100/50/20 mg/l
Te 150/100/50 mg/l
V 100/50/20 mg/l
Wavelengths:

| | |
|---|---|
| Mo | 287.151 nm corr. Sc 424.683 nm |
| | 202.095 nm corr. Sc 424.683 nm |
| | 204.664 nm corr. Sc 424.683 nm |
| | 202.095 nm |
| Nb | 269.706 nm corr. Sc 424.683 nm |
| | 316.240 nm corr. Sc 424.683 nm |
| | 316.340 nm |
| Te | 225.902 nm corr. Sc 335.373 nm |
| | 170.000 nm corr. Sc 335.373 nm |
| | 170.000 nm |
| V | 292.402 nm corr. Sc 424.683 nm |
| | 292.402 nm |
| | 311.071 nm corr. Sc 424.683 nm |

$$w(E^* \text{ in percent}) = \frac{\beta(E^* - \text{measured value in mg/l}) \times V(\text{volumetric flask in l}) \times 100}{m(\text{weight used in mg})}$$

E*=respective element

3. X-Ray Powder Diffraction (XRD)

The X-ray diffraction pattern was produced by X-ray powder diffraction (XRD) and evaluation according to the Scherrer formula.

The diffraction patterns were recorded on a PANalytical Empyrean, equipped with a Medipix PIXcel 3D detector, in θ-θ geometry in an angle range of 2θ=5-70°. The X-ray tube produced Cu—K radiation. The Cu—Kβ radiation was suppressed by use of an Ni filter in the beam path of the incident X-ray beam, so that only Cu—Kα radiation having a wavelength of 15.4 nm (E=8.04778 keV) was diffracted by the sample. The height of the source-side beam path was adapted by means of an automatic divergence slit (programmable divergence slit—PDS) in such a way that the sample was irradiated over a length of 12 mm over the entire angle range. The width of the detector-side X-ray beam was restricted to 10 mm by means of a fixed orifice plate. Horizontal divergence was minimized by use of a 0.4 rad Soller slit.

The height of the detector-side beam path was adapted in a manner analogous to the source-side beam path by means of an automatic anti-scatter slit (programmable anti-scatter slit—PASS) in such a way that the X-ray beam reflected by the sample over a length of 12 mm was detected over the entire angle range.

The samples, depending on the amount available, were prepared either on an amorphous silicon sample plate or tableted as flat-bed samples.

4. STEM

Scanning transmission electron microscopy was carried out on an FEI Titan 80/300 TEM/STEM electron microscope using an acceleration voltage of 300 keV. The spherical aberration was compensated for by means of illumination correction. All high-angle annular dark field (HAADF) images were recorded using a convergence half angle of 17.4 mrad and annular dark field detector half angles of 70-200 mrad. The crystal samples were prepared by means of the microtome technique.

5. SEM

Scanning electron micrographs were recorded on a JEOL JSM-7500F using a secondary electron detector. The acceleration voltage was 2.0 kV and the emission current was 10 µA. The working spacing was about 8 mm.

WORKING EXAMPLES

Example 1

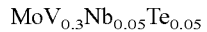

75 ml of twice-distilled water were placed in a 100 ml PTFE beaker, 175.8 mg of monoethylene glycol were added dropwise and 5397.5 mg of $MoO_3$, 1023.3 mg of $V_{25}$, 299.2 mg of $TeO_2$, 274.4 mg of $Nb_2O_5 \cdot xH_2O$ (Nb=63.45% by weight), 540.3 mg of citric acid and 168.5 mg of oxalic acid were subsequently slurried in. The Teflon beaker was closed and transferred into a stainless steel autoclave bomb. This was closed in a pressure-tight manner and clamped onto a horizontal rotating shaft in an oven which had been preheated to 190° C. After 48 hours, the autoclave bomb was taken from the oven and immediately quenched under running water and subsequently cooled in an ice bath for 45 minutes.

The product suspension formed was filtered through a filter paper (pore width 3 μm) and the solid was washed with 200 ml of twice-distilled water.

The product obtained in this way was dried at 80° C. for 16 hours in a drying oven and then ground in a hand mortar.

A yield of solid of 6.8 g was achieved, and the elemental composition of the metals in the product normalized to molybdenum was $MoV_{0.30}Te_{0.05}Nb_{0.05}O_x$, which corresponds to a mass-based composition of 53.0% by weight of Mo, 8.4% by weight of V, 2.9% by weight of Te and 2.3% by weight of Nb.

Scanning transmission electron micrographs of the product are shown in FIGS. 6 and 7.

The BET surface area of the product is 66.4 m²/g, and the product has a pore volume of 0.11 cm³/g and a pore distribution shown in FIG. 8.

Example 2

The catalyst described in example 1 was subjected to a heat treatment in a tube furnace. For this purpose, 1 g of the dried solid was transferred to a porcelain boat so that the bottom of the boat was covered with powder to a height of about 2 mm. Activation was carried out at 600° C. for 2 hours, at a heating rate of 10° C./min in an $N_2$ stream of 100 ml/min. The elemental composition of the metals in the product normalized to molybdenum was: $MoV_{0.30}Te_{0.04}Nb_{0.04}O_x$.

The BET surface area of the product was 25.0 m²/g, and the product had a pore volume of 0.04 cm³/g and a pore distribution shown in FIG. 9.

The XRD of the product is shown in FIG. 2.

Comparative Example 1: ($MoV_{0.3}Nb_{0.1}Te_{0.1}$ from Soluble Precursors)

3.3 l of distilled $H_2O$ were placed in an autoclave (40 l) and heated to 80° C. while stirring. Meanwhile, 725.58 g of ammonium heptamolybdate tetrahydrate (from HC Starck) was introduced and dissolved (AHM solution). In each of three 5 l glass beakers, 1.65 l of distilled $H_2O$ was likewise heated to 80° C. while stirring on a magnetic stirrer with temperature regulation. 405.10 g of vanadyl sulfate hydrate (from GfE, V content: 21.2%), 185.59 g of ammonium niobium oxalate (HC Starck, Nb content: 20.6%) and 94.14 g of telluric acid, respectively, were then introduced into these glass beakers and dissolved (V solution, Nb solution and Te solution).

The V solution, the Te solution and finally the Nb solution were then pumped by means of a peristaltic pump into the AHM solution (pumping time: V solution: 4.5 min at 190 rpm, tube diameter: 8×5 mm, Nb solution: 6 min at 130 rpm, tube diameter: 8×5 mm).

The suspension formed was stirred further at 80° C. for 10 minutes. The speed of the stirrer during the precipitation was 90 rpm. The suspension was subsequently blanketed with nitrogen by building up a pressure up to about 6 bar in the autoclave by means of nitrogen and opening the discharge valve to such an extent that flow under a pressure of $N_2$ occurred through the autoclave (5 minutes). At the end, the pressure was released again to a residual pressure of 1 bar via the venting valve.

The hydrothermal synthesis was carried out at 175° C. for 20 hours in the 40 l autoclave using an anchor stirrer (heating time: 3 hours) at a stirrer speed of 90 rpm.

After the synthesis, the suspension was filtered on a blueband filter by means of a vacuum pump and the filter cake was washed with 5 l of distilled $H_2O$.

Drying was carried out at 80° C. for 3 days in a drying oven and the solid was subsequently milled in an impact mill. The yield of solid achieved was 0.8 kg, and the product was calcined at 280° C. for 4 hours in air (heating rate 5° C./min, air: 1 l/min ).

Activation was carried out in an $N_2$ gas atmosphere in a retort in the furnace at 600° C. for 2 hours (heating rate 5° C./min, $N_2$: 0.5 l/min ). After this treatment, the BET surface area was 13 m²/g.

This gave a catalyst having the stoichiometry $Mo_1V_{0.3}Nb_{0.10}Te_{0.10}O_x$, corresponding to a proportion by weight of the metals based on the total weight of the catalyst of Mo=49% by weight; V=7.9% by weight; Te=6.5% by weight; Nb=4.9% by weight.

The mother liquor after the filtration still contained 0.23% by weight of vanadium and 0.1% by weight of molybdenum.

Comparative Example 2

The catalyst from comparative example 1 was used immediately after the calcination at 280° C. for 4 hours. The calcination at 600° C. under nitrogen for 2 hours was not carried out.

Example 3

The catalytic activity of the catalysts of example 1 and comparative examples 1 and 2 in the oxidative dehydrogenation of ethane was examined in the temperature range from 330° C. to 420° C. at atmospheric pressure in a tube reactor. For this purpose, 25 mg (example 1 and comparative example 1) or 200 mg (comparative example 2) of catalyst (particle size 150-212 μm) were in each case diluted with silicon carbide (particle size from 150 to 212 μm) in a mass ratio of 1:5. A layer of 250 mg of silicon carbide of the same particle size was introduced both below and above the catalyst bed and the ends of the tube reactor were closed by means of silica wool plugs.

The reactor was flushed with inert gas before commencement of the experiment and subsequently heated to 330° C. under a helium flow of 50 sccm. After the desired temperature had been reached and was stable for 1 hour, the gas fed in was switched over to the reaction gas mixture.

The inlet gas composition was $C_2H_6/O_2/He$=9.1/9.1/81.8 (v/v) at a total volume flow of 50 sccm.

Analysis of the product gas stream was carried out in a gas chromatograph equipped with Haysep N and Haysep Q columns, a 5A molecular sieve column and a thermal conductivity detector.

The ethylene formation rates under the above-described conditions are shown in FIG. 11. In the measurement of comparative example 1, 200 mg of catalyst instead of 25 mg were used because the catalyst of the invention was so much more active that the activity could not be measured using the same mass flow regulators and the same amount of catalyst.

However, the graph in FIG. 11 is normalized to the space velocity so that the values are comparable.

Example 4

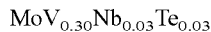

75 ml of twice-distilled water were placed in a 100 ml PTFE beaker, 180.3 mg of monoethylene glycol were added dropwise and 5399.9 mg of $MoO_3$, 1024.0 mg of $V_2O_5$, 180.2 mg of $TeO_2$, 166.8 mg of $Nb_2O_5 \cdot xH_2O$ (Nb=63.45% by weight), 542.4 mg of citric acid and 101.3 mg of oxalic acid were subsequently slurried in. The Teflon beaker was closed and transferred into a stainless steel autoclave bomb. This was closed in a pressure-tight manner and clamped on a horizontal rotating shaft in an oven which had been preheated to 190° C. After 48 hours, the autoclave bomb was taken from the oven and immediately quenched under running water and subsequently cooled in an ice bath for 45 minutes.

The product suspension formed was filtered through a filter paper (pore width 3 μm) and the solid was washed with 200 ml of twice-distilled water.

The product obtained in this way was dried at 80° C. for 16 hours in a drying oven and then ground in a hand mortar.

Example 5

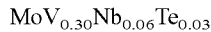

75 ml of twice-distilled water were placed in a 100 ml PTFE beaker, 182.3 mg of monoethylene glycol were added dropwise and 5406.7 mg of $MoO_3$, 1023.1 mg of $V_2O_5$, 177.7 mg of $TeO_2$, 329.9 mg of $Nb_2O_5 \cdot xH_2O$ (Nb=63.45% by weight), 543.4 mg of citric acid and 204.5 mg of oxalic acid were subsequently slurried in. The Teflon beaker was closed and transferred into a stainless steel autoclave bomb. This was closed in a pressure-tight manner and clamped on a horizontal rotating shaft in an oven which had been preheated to 190° C. After 48 hours, the autoclave bomb was taken from the oven and immediately quenched under running water and subsequently cooled in an ice bath for 45 minutes.

The product suspension formed was filtered through a filter paper (pore width 3 μm) and the solid was washed with 200 ml of twice-distilled water.

The product obtained in this way was dried at 80° C. for 16 hours in a drying oven and then ground in a hand mortar.

Example 6

The catalytic activity of the catalysts of examples 4 and 5 in the oxidative dehydrogenation of ethane was examined in the temperature range 330-420° C. at atmospheric pressure in a tube reactor. For this purpose, 50 mg of catalyst (particle size 150-212 μm) were in each case diluted with silicon carbide (particle size 150-212 μm) in a mass ratio of 1:5. A layer of 250 mg of silicon carbide of the same particle size was introduced both below and above the catalyst bed and the ends of the tube reactor were closed by means of silica wool plugs.

The reactor was flushed with inert gas before commencement of the experiment and subsequently heated to 330° C. under a helium flow of 50 sccm. After the desired temperature had been reached and was stable for 1 hour, the gas fed in was switched over to the reaction gas mixture.

The inlet gas composition was $C_2H_6/O_2/He$=9.1/9.1/81.8 (v/v) at a total volume flow of 50 sccm.

Analysis of the product gas stream was carried out in a gas chromatograph equipped with Haysep N and Haysep Q columns, a 5A molecular sieve column and a thermal conductivity detector.

The ethylene formation rates under the above-described conditions are shown in FIG. 12.

TABLE 1

| | Calc. 600° C./$N_2$ | Composition | BET [m$^2$/g] | Pore volume [cm$^3$/g] |
|---|---|---|---|---|
| Example 1 | No | $MoV_{0.3}Nb_{0.05}Te_{0.05}O_x$ | 60.4 | 0.11 |
| Example 2 | Yes | $MoV_{0.3}Nb_{0.05}Te_{0.05}O_x$ | 25 | 0.04 |
| Example 4 | No | $MoV_{0.3}Nb_{0.03}Te_{0.03}O_x$ | 38.1 | 0.11 |
| Example 5 | No | $MoV_{0.3}Nb_{0.06}Te_{0.03}O_x$ | 69.4 | 0.13 |
| Comp. example 1 | Yes | $MoV_{0.3}Nb_{0.1}Te_{0.1}O_x$ | 13 | 0.03 |
| Comp. example 2 | No | No M1 phase | | |

Table 1 shows the stoichiometries and the BET surface areas of the catalysts according to the invention together with comparative examples.

The invention claimed is:

1. A mixed oxide material comprising the elements molybdenum, vanadium, niobium and tellurium which in the XRD using Cu-Ka radiation has diffraction reflections h, i, k and l whose peaks are approximately at the diffraction angles (2θ) 26.2°±0.5° (h), 27.0°±0.5° (i), 7.8°±0.5° (k) and 28.0°±0.5° (I), said mixed oxide material having the following stoichiometry:

$$Mo_1 V_a Nb_b Te_c O_n \quad (I)$$

a=0.2 to 0.35,
b=greater than 0 to 0.08,
c=greater than 0 to 0.08,
n=an integer determined by the valence and abundance of the elements other than oxygen in (I).

2. The mixed oxide material as claimed in claim 1, wherein said mixed oxide material has a BET surface area which is greater than 15 m$^2$/g.

3. A process for producing a mixed oxide material as claimed in claim 1, comprising the steps:
a) production of a mixture of starting compounds containing molybdenum, vanadium, niobium and a tellurium-containing starting compound in which tellurium is present in the oxidation state +4, oxalic acid and at least one further oxo ligand,
b) hydrothermal treatment of the mixture of starting compounds at a temperature of from 100° C. to 300° C. to give a product suspension,
c) isolation and drying of the mixed oxide material present in the suspension resulting from step b).

4. The process as claimed in claim 3, wherein the tellurium-containing starting compound is tellurium dioxide or a compound of the formula $Mx^{n+}TeO_3$ where n=1 or 2 and x=2/n, where M is an alkali metal or alkaline earth metal.

5. The process as claimed in claim 3, wherein the mixture of starting compounds is present as aqueous suspension.

6. The process as claimed in claim 3, wherein the mixture of starting compounds contains a dicarboxylic acid, a dial or another compound having two hydroxy groups in adjacent positions as further oxo ligand.

7. The process as claimed in claim 3, wherein the mixture of starting compounds contains molybdenum trioxide.

8. The process as claimed in claim 3, wherein the mixture of starting compounds contains vanadium pentoxide.

9. The process as claimed in claim 3, wherein the mixture of starting compounds contains citric acid as further oxo ligand.

10. The process as claimed in claim 3, wherein the mixture of starting compounds contains citric acid and glycol as further oxo ligands.

11. The process as claimed in claim 3, wherein the drying in step c) is carried out at from 50° C. to 400° C.

12. The process as claimed in claim 3, wherein the drying in step c) is carried out in two steps, firstly at from 50° C. to 150° C. and then at from 350° C. to 400° C.

13. The process as claimed in claim 3, wherein drying is followed by activation at from 500° C. to 650° C. under inert gas.

14. The process as claimed in claim 3, wherein the mixed oxide material present in the suspension resulting from step b) has, in the XRD using Cu-Kα radiation, diffraction reflections h, i, k and l whose peaks are approximately at the diffraction angles (2θ) 26.2°±0.5° (h), 27.0°±0.5° (i), 7.8°±0.5° (k) and 28.0° ±0.5° (l).

15. A process for the oxidative dehydrogenation of ethane to ethene, the method comprising contacting ethane with the mixed oxide material as claimed in claim 1.

16. A process for the oxidation of propane to acrylic acid, the method comprising oxidizing the propane while in contact with the mixed oxide material as claimed in claim 1.

17. A process for the ammoxidation of propane by means of ammonia to acrylonitrile, the method comprising contacting the propane and the ammonia with the mixed oxide material as claimed in claim 1.

* * * * *